United States Patent
Hershey et al.

(10) Patent No.: US 9,242,085 B2
(45) Date of Patent: Jan. 26, 2016

(54) TRANSCUTANEOUS ELECTRICAL STIMULATION FOR TREATING NEUROLOGICAL DISORDERS

(71) Applicant: BOSTON SCIENTIFIC NEUROMODULATION CORPORATION, Valencia, CA (US)

(72) Inventors: Bradley L. Hershey, Valencia, CA (US); Tamara C. Baynham, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/312,066

(22) Filed: Jun. 23, 2014

(65) Prior Publication Data
US 2015/0005852 A1    Jan. 1, 2015

Related U.S. Application Data

(60) Provisional application No. 61/841,199, filed on Jun. 28, 2013.

(51) Int. Cl.
*A61N 1/00* (2006.01)
*A61N 1/04* (2006.01)
*A61N 1/36* (2006.01)

(52) U.S. Cl.
CPC .......... *A61N 1/0456* (2013.01); *A61N 1/36014* (2013.01); *A61N 1/36021* (2013.01)

(58) Field of Classification Search
CPC ............ A61N 1/0456; A61N 1/36014; A61N 1/36021
See application file for complete search history.

(56) References Cited

U.S. PATENT DOCUMENTS

| | | | |
|---|---|---|---|
| 6,516,227 B1 | 2/2003 | Meadows et al. | |
| 6,993,384 B2 | 1/2006 | Bradley et al. | |
| 2007/0299482 A1* | 12/2007 | Littlewood et al. | 607/46 |
| 2011/0276112 A1 | 11/2011 | Simon et al. | |
| 2012/0029591 A1 | 2/2012 | Simon et al. | |
| 2012/0029601 A1 | 2/2012 | Simon et al. | |
| 2012/0101326 A1 | 4/2012 | Simon et al. | |
| 2013/0304152 A1 | 11/2013 | Bradley et al. | |

OTHER PUBLICATIONS

U.S. Appl. No. 61/646,773, System and Method for Shaped Phased Current Deilivery, Inventor: Kerry Bradley, et al., filing date: May 14, 2012.

* cited by examiner

*Primary Examiner* — George Manuel
(74) *Attorney, Agent, or Firm* — Schwegman Lundberg & Woessner P.A.

(57) ABSTRACT

A method for treating a disorder of a patient. The method comprises transcutaneously delivering electrical energy to a targeted tissue site at a frequency of at least 50 KHz, thereby treating the disorder.

20 Claims, 3 Drawing Sheets

TRANSCUTANEOUS ELECTRICAL STIMULATION FOR TREATING NEUROLOGICAL DISORDERS

RELATED APPLICATION DATA

The present application claims the benefit under 35 U.S.C. §119 to U.S. Provisional Patent Application No. 61/841,199, filed Jun. 28, 2013. The foregoing application is hereby incorporated by reference into the present application in its entirety.

TECHNICAL FIELD

The present disclosure relates to systems and methods for transcutaneously treating neurological disorders in patients.

BACKGROUND OF THE INVENTION

Transcutaneous electrical nerve stimulation (TENS) is a known non-invasive technique extensively used by numerous health-care providers worldwide. TENS uses an electrical current to stimulate nerves and acupuncture points across the surface of the skin. Due to its simplicity, TENS can be administered either in clinics by health-care professionals or at home by patients through various TENS devices available in the market. Its ease of use, general safety and portability make it a preferred treatment over a long term use of medications and nerve blocks for chronic pain.

A variety of TENS techniques which differ in terms of specific modalities of treatment are known. Few examples of these techniques include acupuncture-like TENS (ALTENS) and Intense TENS, which are typically applied to stimulate nerves for pain relief. These modalities are characterized based on various parameters, such as pulse frequency, pulse amplitude, pulse duration, analgesic effects, pulse pattern, etc.

Although TENS techniques are generally successful for non-invasively stimulating nerves within a patient's body, due to the relatively high impedance of the skin and underlying tissue, TENS techniques are limited to stimulating nerves near the surface of the skin. In order to overcome the high impedance of the tissue, the amplitude of the electric current can be theoretically increased to treat nerves that are deeper in the body. However, such an increase in amplitude may cause tissue heating, and thus, pain to the patient.

It may therefore be beneficial to provide methods to provide or otherwise enable such treatments, but which are non-invasive, reduce tissue heating and yield intended therapeutic effect(s) for treatment of disorders of the patient.

SUMMARY OF THE INVENTION

In accordance with the present inventions, a method for treating a disorder of a patient is provided. The disorder may be, e.g., asthma, skin cancer, alopecia, irritable bowel syndrome, inflammatory bowel disease, diabetes, multiple sclerosis, amyotrophic lateral sclerosis (ALS), high cholesterol, overactive bladder, migraine, headache, fibromyalgia, complex region pain syndrome (I and II), angina, arthritis, leprosy, or chronic pain. The method comprises transcutaneously delivering electrical energy (e.g., an electrical pulse train) to a targeted tissue site at a frequency of at least 50 KHz, and perhaps at least 100 KHz, thereby treating the disorder. The target tissue site may be at least 2 cm, but perhaps not more than 4 cm, beneath the skin of the patient. The stimulation energy may be applied by a patch electrode affixed to the skin of the patient.

Other and further aspects and features of the invention will be evident from reading the following detailed description of the preferred embodiments, which are intended to illustrate, not limit, the invention.

BRIEF DESCRIPTION OF DRAWINGS

The drawings illustrate some embodiments of the present disclosure, in which similar elements are referred to by common reference numerals. In order to better appreciate how the above-disclosed and other advantages and objects of the present disclosure are obtained; a more particular description of the present disclosure briefly described above will be rendered by reference to specific embodiments thereof, which are illustrated in the accompanying drawings. Understanding that these drawings depict only typical embodiments of the disclosure and are not therefore to be considered limiting of its scope, the disclosure will be described and explained with additional specificity and detail through the use of the accompanying drawings in which.

DETAILED DESCRIPTION

Figure 1:
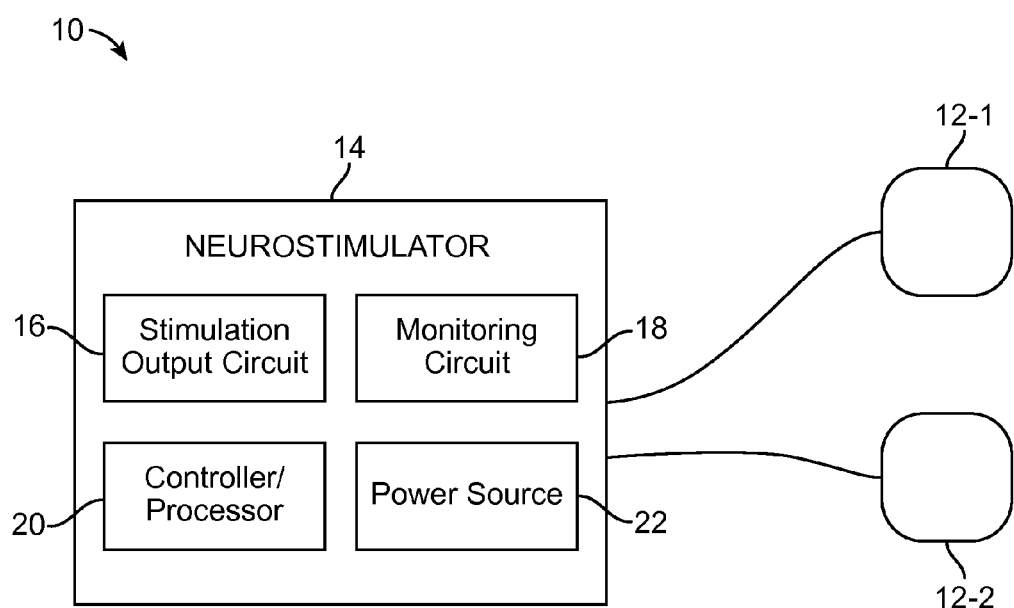
FIG. 1 is a plan view of an exemplary transcutaneous neurostimulation system, according to an embodiment of the present disclosure.

Turning first to FIG. 1, an exemplary transcutaneous neurostimulation system 10 will be described. The system 10 includes patch electrodes 12-1 and 12-2 (collectively, electrodes 12) and a neurostimulator 14. The patch electrodes 12 may store an electrically conducting medium, such as various known, related art and/or later developed hydrophilic materials and hydrogels, and configured to release the medium from a side that is to be placed in communication with a patient's skin. Alternatively, this electrically conductive medium may be applied separately between the electrodes 12 and the skin.

The neurostimulator 14 generally includes a stimulation output circuit 16, a monitoring circuit 18, a controller/processor 20, and a power source 22. The stimulation output circuit 16 is configured to generate electrical stimulation energy in accordance with a relatively high rate electrical pulse train to treat a disorder. Alternatively, a relatively high frequency continuous stimulation waveform, e.g., sinusoidal waveform, may be generated by the stimulation output circuit 16 in a manner as disclosed in U.S. Provisional Patent Application Ser. No. 61/646,773, entitled "System and Method for Shaped Phased Current Delivery," which is expressly incorporated herein by reference in its entirety.

The pulse rate of the electrical pulse train may be controlled either alone or in any combination with a set of other stimulation parameters. Exemplary stimulation parameters include, but are not limited to, electrode combinations, which define the electrodes that are activated as anodes (positive), cathodes (negative), and turned off (zero), and percentage of stimulation energy assigned to each electrode 12 of the array of electrodes (fractionalized electrode configurations), and electrical pulse parameters, which define pulse width (measured in microseconds), and/or burst rate (measured as the stimulation ON duration X and stimulation OFF duration Y).

The stimulation output circuit 16 may include a variety of architectures for delivering electrical stimulation energy. In one example, the stimulation output circuit 16 may include independently controlled current sources for providing stimulation pulses of specified and known amperage to or from the electrodes 12. In another example, the output circuit 16 may include independently controlled voltage sources for providing stimulation pulses of a specified and known voltage at the electrodes 12 or to multiplexed current or voltage sources that are then connected to the electrodes 12. The operation of this stimulation output circuit 16, including alternative embodiments of suitable output circuit(s) for performing the same or similar function of generating stimulation pulses of a prescribed amplitude and width, is disclosed more fully in U.S. Pat. Nos. 6,516,227 and 6,993,384, which are expressly incorporated herein by reference in their entireties. The electrical stimulation energy generated by the stimulation output circuit 16 is output to the electrodes 12.

The monitoring circuit 18 is configured to monitor the status of various nodes or other points throughout the system 10, e.g., power supply voltages, temperature, battery voltage, etc. In some embodiments, the monitoring circuit 18 may monitor changes in various physiological parameters at and/or around the stimulation area adjacent to the electrodes 12 by using the electrodes 12 as sensors or a separate sensor (not shown) located in the patient's body. Exemplary physiological parameters include, but are not limited to, blood pressure, acidic concentration, and/or temperature.

The controller/processor 20 is configured for obtaining status data from the monitoring circuit 18 and controlling the stimulation output circuit 16 to output the stimulation energy in accordance with the stimulation parameters. In the illustrated embodiment, the controller/processor 20 manages the neurostimulation therapy based on a user input received through a user interface (not shown) of the neurostimulation system 10. Alternatively or additionally, the controller/processor 20 may be configured for managing the neurostimulation therapy based on changes in the physiological parameters sensed at or around the electrodes 12 and monitored by the monitoring circuit 18.

The power source 22 includes a mains power supply for powering the neurostimulator 14. The power source 22 generates various voltages, some of which are regulated and some of which are not, as needed by the various circuits located within the system 10. The system 10 may receive the control and status signals from the controller/processor 20, and accordingly generate electrical stimulation energy, which is delivered transcutaneously to a target tissue site, or to a target nerve, for treating a disorder.

During operation, the patch electrodes 12 are affixed to the skin at a location adjacent to a target tissue, or target nerve, for treating the disorder. Electrical stimulation energy is delivered to the electrodes 12 from the stimulation output circuit 16 to transcutaneously stimulate the target nerve. This type of transcutaneous electrical stimulation of the target nerve may induce pain or become relatively uncomfortable for the patient. In order to improve or otherwise enhance the patient's therapy experience, anesthesia may be applied on the skin at the area of stimulation on the skin. At and/or around the stimulation area adjacent to the electrodes 12, the patient's skin may be coated with a variety of known, related art or later developed analgesic, prophylactic and/or curative gels or pastes, before and/or after delivering the electrical stimulation energy to the electrodes 12. This procedure may reduce or even avoid skin damage and/or minimize, or avoid pain experienced by the patient.

Electrical energy will be delivered between the electrodes 12, so that the electrical current has a path from the stimulation output circuit 16 to the target nerve and a sink path from the target nerve to the stimulation output circuit 16. Electrical energy may be transmitted to the target nerve in a monopolar or a bipolar fashion, or by any other manner available depending on the available number of electrodes for operation.

Monopolar delivery occurs when a selected electrode, such as the patch electrode 12-1, is activated along with the other patch electrode, such as the electrode 12-2, behaving as a ground electrode so that electrical energy is transmitted between the selected electrode 12-1 and the ground electrode 12-2. The selected electrode 12-1 is placed transcutaneously adjacent to the target nerve, for e.g., vagus nerve, and the ground electrode 12-2 is placed on the body far away from the target nerve. For e.g., the ground electrode 12-2 may be placed transcutaneously around abdomen or leg of the patient. Monopolar delivery may also occur when one or more of the electrodes 12 are activated along with a large group of lead electrodes (not shown) located remotely from the electrode(s) 12 so as to create a monopolar effect; that is, electrical energy delivered by the stimulation output circuit 16 is conveyed from the electrode(s) 12 in a relatively isotropic manner. Bipolar delivery occurs when two of the electrodes 12-1 and 12-2 are activated as anode and cathode respectively, so that electrical energy is transmitted between the electrodes 12. In this case, both the electrodes 12 are located adjacent to the target nerve.

Significantly, the stimulation output circuit 16 delivers the electrical stimulation energy at a substantially high frequency of at least 50 KHz or more, such as 100 KHz, to stimulation the target nerve, which may be located 2 cm or more, such as 4 cm, beneath the skin. The high frequency of the electrical stimulation energy reduces impedance of the skin, thereby decreasing the amplitude of current needed to penetrate the skin and underlying tissue to reach the target nerve, and preventing heating or damage to the skin and underlying tissue. While the stimulation output circuit 16 delivers the electrical stimulation energy to the electrodes 12, the monitoring circuit 18 optionally monitors induced changes in the physiological parameters at and/or around the stimulation area adjacent to the electrodes 12. If any of the physiological parameters, such as blood pressure, acidic concentration, and/or heat, at or around the stimulation area exceed their respective threshold values, then the controller/processor 20 may automatically deactivate the stimulation output circuit 16, which stops the delivery of electrical stimulation energy to the electrodes 12. Alternatively, the stimulation output circuit 16 may be deactivated through a user input (manually) in response to perceived pain by the patient.

Figure 2:
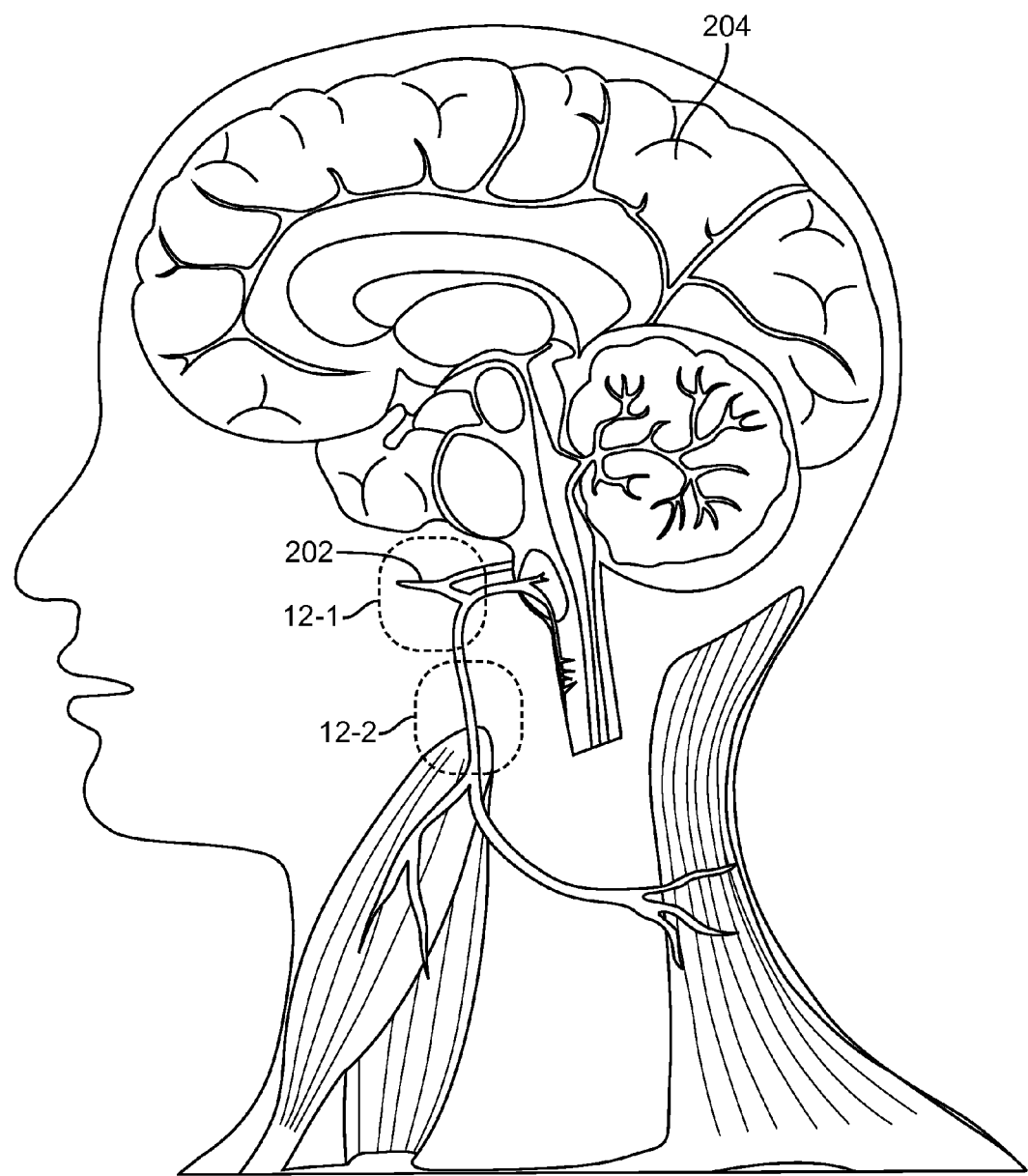
FIG. 2 is a plan view that illustrates an exemplary placement of electrodes of the neurostimulation system of FIG. 1 for treatment of asthma, according to an embodiment of the present disclosure.

The transcutaneous stimulation system 10 may be used to treat a variety of disorders. In one example, the system 10 is used to treat asthma by stimulating the vagus nerve 202, as shown in FIG. 2. The vagus nerve 202 is a parasympathetic nerve, which includes both motor and sensory fibers and passes from the brain 204 through the neck and thorax to the abdomen. The vagus nerve 202 descends behind the root of the lungs (not shown), where the nerve 202 spreads out to form posterior pulmonary plexus, whose branches accompany the ramifications of the bronchi through the lung tissue. If the patient is suffering from asthma, the vagus nerve 202 is hypersensitive to external stimuli, such as dust, smoke, and pollen, which cause the airway to narrow and produce excess mucus, leading to the patient experiencing difficulty in breathing. Electrical stimulation energy may therefore be applied to the vagus nerve 202 to provide a therapeutic effect relative to asthma and reduce constriction of the airway.

The electrodes 12 are placed near, adjacent and/or around a patient's ear, to reduce the possibility of accidently or unintentionally stimulating other nerves, such as phrenic nerve controlling respiration. Specifically, the electrodes 12 can be affixed to the skin in order to transcutaneously stimulate the vagus nerve 202, which is relatively deeper from the skin at a location near or around the ear.

During operation, once the electrodes 12 are positioned over the skin adjacent to the vagus nerve 202, the stimulation output circuit 16 may be activated to apply the electrical stimulation energy to the electrodes 12. As disclosed above, this electrical stimulation energy is of a substantially high frequency for transcutaneously stimulating the vagus nerve 202.

As mentioned above, this high frequency allows the electrical stimulation energy to reduce the impedance of the skin and penetrate deeper within the body. In fact, the electrical stimulation energy is able to reach the vagus nerve 202 without significant heating of the skin and underlying tissue. Further, the high frequency of the electrical stimulation therapy prevents the need of increasing the pulse amplitude of the electrical stimulation energy to reach a target tissue, such as the vagus nerve 202. As a result, relatively less charge (current amplitude×pulse width) or charge density (charge per unit area of the tissue) is transferred to the target tissue such as the vagus nerve 202 during therapy and thus minimizes tissue heating. The electrical stimulation energy may also have a low duty cycle so that the charge or charge injected per second (current amplitude×pulse width×rate (or period)) is reduced to enable a relatively safer therapeutic regime.

The frequency of the electrical stimulation energy may be selected based on the depth of the vagus nerve 202. For example, if the depth of the vagus nerve 202 is 2 cm beneath the skin at a location around the ear of the patient, the frequency of the electrical stimulation energy may be set at a lower frequency (e.g., 50 KHz). If the depth of the vagus nerve 202 is 4 cm beneath the skin at a location around the ear of the patient, the frequency of the electrical stimulation energy may be set at a higher frequency (e.g., 100 KHz). Thus, in general, the greater the depth of the vagus nerve 202, the greater the frequency of the applied electrical stimulation energy should be.

Upon perception of pain during treatment of the disorder, in response to user input, the amplitude of applied electrical stimulation energy may be reduced by the stimulation output circuit 16 to prevent tissue heating, and the frequency of the applied electrical stimulation energy may be increased by the stimulation output circuit 16 to reduce the tissue impedance, so that the decreased electrical stimulation energy reaches the vagus nerve 202. Similarly, the stimulation output circuit 16 may automatically reduce the amplitude and increase the frequency of the applied electrical stimulation energy if the controller/processor 20 determines that a physiological parameter at or around the stimulation area has exceeded a predetermined threshold value to avoid the patient from experiencing pain during therapy. The electrical stimulation energy may be applied to the electrodes 12 multiple times at regular intervals, or alternatively spread across multiple sessions for a predefined period of time.

Figure 3:
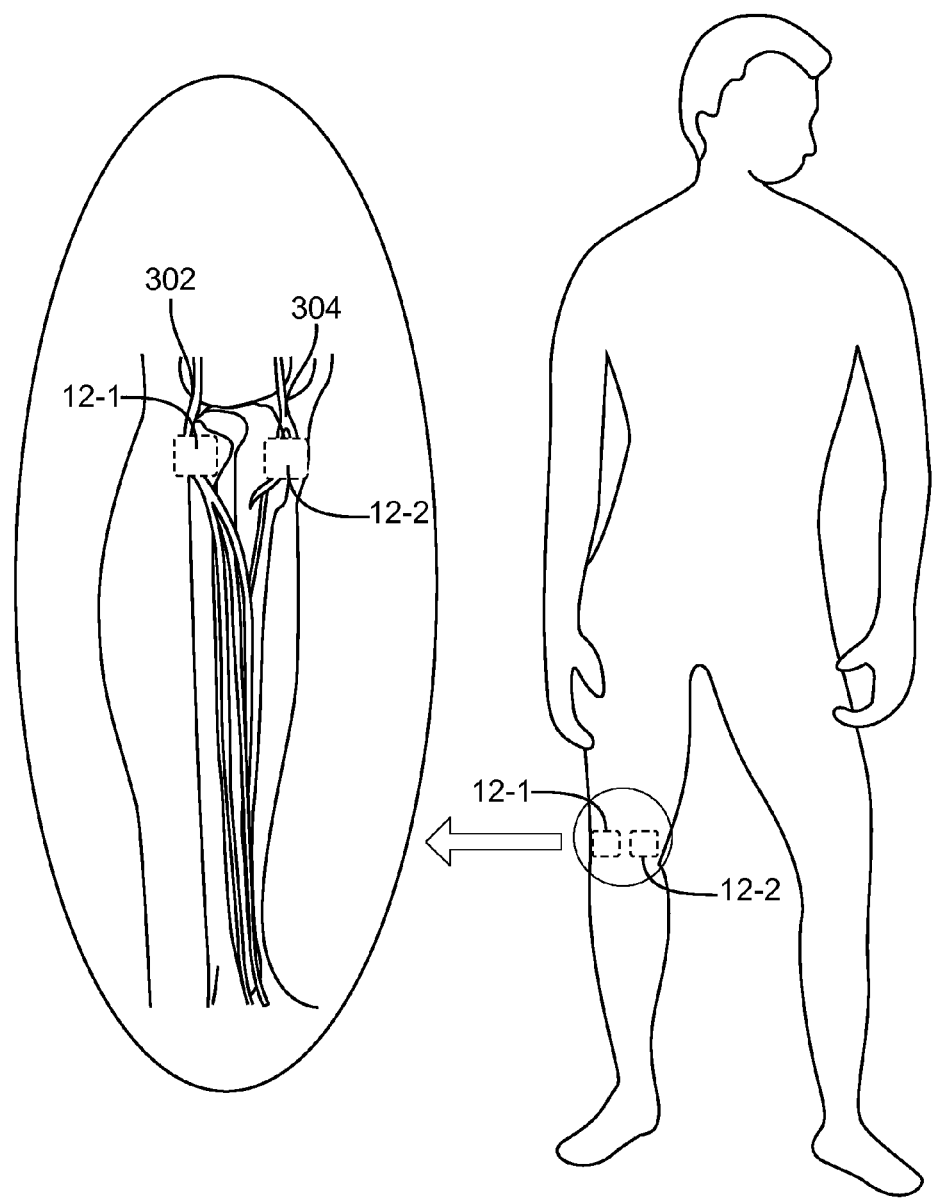
FIG. 3 is a plan view that illustrates an exemplary placement of electrodes of the neurostimulation system of FIG. 1 for treatment of arthritis, according to another embodiment of the present disclosure.

In another example shown in FIG. 3, the system 10 may be used for treating arthritis in a patient's knee by stimulating nerves, such as the common peroneal nerve 302 and saphenous nerve 304. The patch electrodes 12 may be affixed to the skin over the knee, and provided with electrical stimulation energy at a substantially high frequency. As discussed above with respect to the vagus nerve, the frequency of the applied electrical stimulation can be set based on the depth of the nerves 302, 304. Furthermore, in the case where the patient experiences pain, the amplitude of the applied electrical stimulation energy may be reduced and the frequency of the applied electrical stimulation energy may be increased, as discussed above with respect to FIG. 2. Also, the electrical stimulation energy may be applied to the electrodes 12 multiple times at regular intervals, or alternatively spread across multiple sessions for a predefined period of time, as described above with respect to FIG. 2, in order to treat arthritis.

In addition to the above methods, various neurological disorders may be treated by the disclosed transcutaneous stimulation of target tissue at a substantially high frequency. Examples of these neurological disorders include, but are not limited to, skin cancer, alopecia, irritable bowel syndrome, inflammatory bowel disease, diabetes, multiple sclerosis, amyotrophic lateral sclerosis (ALS), high cholesterol, overactive bladder, migraine, headache, fibromyalgia, complex region pain syndrome (I and II), angina, arthritis, leprosy, and/or chronic pain.

Although particular embodiments of the present disclosure have been shown and described, it will be understood that it is not intended as limiting to the disclosed embodiments, and it will be obvious to those skilled in the art that various changes and modifications may be made without departing from the spirit and scope of the present inventions. Thus, the various embodiments are intended to cover alternatives, modifications, and equivalents, which may be included within the spirit and scope of the present inventions as defined by the claims.

What is claimed is:

1. A method for treating a disorder of a patient, the method comprising:
    transcutaneously delivering electrical energy to a targeted tissue site at an amplitude and at a frequency of at least 50 KHz, thereby treating the disorder; and
    responding to a user input during treatment of the disorder that indicates perception of pain by decreasing the amplitude of the electrical energy and increasing the frequency of the electrical energy.

2. The method of claim 1, wherein the frequency is at least 100 KHz.

3. The method of claim 1, wherein the targeted tissue site is at least 2 cm beneath the skin of the patient.

4. The method of claim 1, wherein the targeted tissue site is not more than 4 cm beneath the skin of the patient.

5. The method of claim 1, wherein the delivered electrical energy comprises an electrical pulse train.

6. The method of claim 1, wherein the delivered electrical energy reduces an impedance of the skin of the patient.

7. The method of claim 1, wherein the disorder includes asthma.

8. The method of claim 1, further comprising affixing a patch electrode to the skin of the patient, wherein the electrical energy is delivered by the patch electrode.

9. The method of claim 1, wherein the disorder includes skin cancer.

10. The method of claim 1, wherein the disorder includes alopecia.

11. The method of claim 1, wherein the disorder includes irritable bowel syndrome or inflammatory bowel disease.

12. The method of claim 1, wherein the disorder includes diabetes.

13. The method of claim 1, wherein the disorder includes multiple sclerosis.

14. The method of claim 1, wherein the disorder includes amyotrophic lateral sclerosis (ALS).

15. The method of claim 1, wherein the disorder includes high cholesterol.

16. The method of claim 1, wherein the disorder includes overactive bladder.

17. The method of claim 1, wherein the disorder includes migraine or headache.

18. The method of claim 1, wherein the disorder includes angina.

19. The method of claim 1, wherein the disorder includes arthritis.

20. The method of claim 1, wherein the disorder includes fibromyalgia, complex region pain syndrome (I and II), leprosy or chronic pain.

* * * * *